United States Patent [19]

Okamoto et al.

[11] Patent Number: 4,963,585
[45] Date of Patent: Oct. 16, 1990

[54] COMPOUND, WF11605 AND DERIVATIVE THEREOF

[75] Inventors: Masanori Okamoto; Eisaku Tsujii; Tsutomu Kaizu; Hiroshi Hatanaka; Masakuni Okuhara; Kozo Sawada; Hirokazu Tanaka, all of Tsukuba, Japan

[73] Assignee: Fujisawa Pharmaceutical Company, Ltd., Osaka, Japan

[21] Appl. No.: 310,323

[22] Filed: Feb. 14, 1989

[30] Foreign Application Priority Data

Feb. 15, 1988 [GB] . United Kingdom ............ 8803426

[51] Int. Cl.$^5$ .......... A61K 31/19; A61K 31/70; C07C 69/74; C07H 15/24
[52] U.S. Cl. ............................... 514/529; 562/498; 562/403; 560/256; 560/116; 536/18.1; 536/16.8; 514/557; 514/548; 514/34
[58] Field of Search ................ 536/16.8, 18.1; 560/116, 256; 562/498, 403; 514/34, 529, 557, 548

[56] References Cited

U.S. PATENT DOCUMENTS 4,621,137 11/1986 Miyake et al. .............. 536/18.1

FOREIGN PATENT DOCUMENTS 1618224  3/1971  Fed. Rep. of Germany .
1926010 10/1972  Fed. Rep. of Germany .
2063596  8/1976  Fed. Rep. of Germany .
1211806 11/1969  United Kingdom .
1205012  9/1970  United Kingdom .

OTHER PUBLICATIONS

Patent Abstracts of Japan, vol. 10, No. 258 (C-370)(2314), Sep. 4, 1986.

Patent Abstracts of Japan, vol. 11, No. 80 (C-409)(2527) Mar. 11, 1987.

Primary Examiner—Nicky Chan
Attorney, Agent, or Firm—Oblon, Spivak, McClelland, Maier & Neustadt

[57] ABSTRACT

The invention relates to a compound of antimicrobial activity of the formula

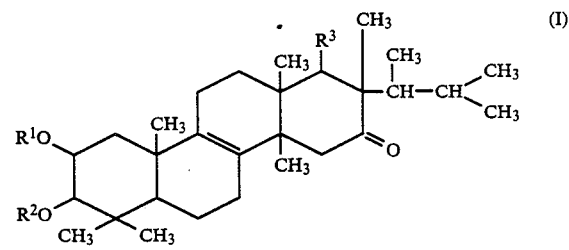

wherein
$R^1$ is hydrogen or lower alkanoyl,
$R^2$ is hydrogen or

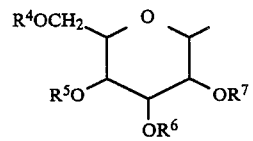

in which
$R^4$, $R^5$, $R^6$ and $R^7$ are hydrogen or lower alkanoyl,
$R^3$ is carboxy or a protected carboxy, and pharmaceutically acceptable salt thereof.

5 Claims, No Drawings

COMPOUND, WF11605 AND DERIVATIVE THEREOF

This invention relates to a new compound, WF11605, and derivative thereof. More particularly, it relates to a new compound, WF11605, derivative thereof and pharmaceutically acceptable salt thereof which have antimicrobial activity and are highly potent antagonists of Leukotriene B$_4$ (LTB$_4$) and therefore useful as antibiotics and agent for the prevention and treatment of diseases caused by LTB$_4$, to a process for the prepartion thereof and to a pharmaceutical composition comprising the same.

The inventors of this invention has succeeded in isolating a new compound WF11605 from the cultured broth of a newly-isolated microorganism, Agonomycetes strain F-11605, found that WF11605 possesses antimicrobial activity and is highly potent antagonist of LTB$_4$ in the result of various investigations, and succeeded in producing synthetic derivatives thereof after identification of the chemical structure of WF11605.

The WF11605 and derivatives thereof of this invention can be represented by the following formula:

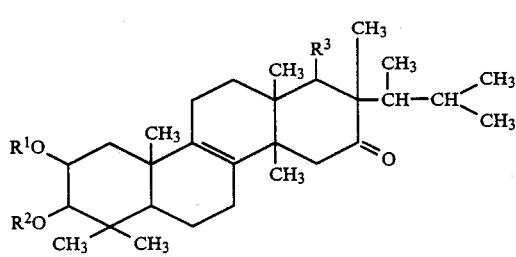

wherein
R$^1$ is hydrogen or acyl,
R$^2$ is hydrogen or

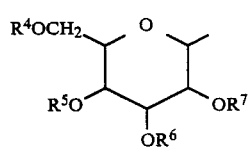

in which
R$^4$, R$^5$, R$^6$ and R$^7$ are hydrogen or acyl,
R$^3$ is carboxy or protected carboxy,
and pharmaceutically acceptable salt thereof.

The pharmaceutically acceptable salt of the compound (I) may include an inorganic or organic base salt (e.g. sodium salt, potassium salt, triethylamine salt, etc.), a salt with an amino acid (e.g. arginine salt, lysine salt, etc.) and the like.

The WF11605 obtained in the Example as mentioned below has the following physicochemical properties as its free form.

(1) Appearance: colorless needle
(2) Molecular weight: 692, FAB-MS m/z 715 (M+Na)$^+$
(3) Molecular formula: C$_{38}$H$_{60}$O$_{11}$
(4) Elemental analysis: Found: C 64.49, H 8.49 Calcd for C$_{38}$H$_{60}$O$_{11}$·H$_2$O: C64.20, H 8.79
(5) Color reaction:
positive: Molish, I$_2$ vapour, CeSO$_4$
negative: FeCl$_3$, ninhydrin, Dragendorff reagent
(6) Solubility:
sparingly soluble: H$_2$O, methanol, ethanol
insoluble: chloroform, ether
(7) Melting point: 291° C. (dec.)
(8) Specific rotation: $[\alpha]_D^{23} -46°$ (c=0.5, CH$_3$OH)
(9) Ultraviolet absorption spectrum: end absorption

| (10) Thin layer chromatography: | |
|---|---|
| CHCl$_3$—CH$_3$OH—CH$_3$COOH (200-40-1, V/V) | Rf 0.56 |
| n-C$_4$H$_9$OH—CH$_3$COOH—H$_2$O (4-1-2, V/V) | Rf 0.83 |
| | (silica gel plate) |

(11) Infrared absorption spectrum: $\nu_{max}^{KBr}$ 3400, 2940, 1730, 1710, 1700, 1640, 1460, 1450, 1430, 1380, 1360, 1250, 1150, 1120, 1090, 1070, 1040, 1020, 980, 950, 890 cm$^{-1}$

| (12) $^1$H-Nuclear magnetic resonance spectrum: δ (400 MHz, CD$_3$OD - CDCl$_3$ (1:1)) | |
|---|---|
| 5.14 | (1H, m), |
| 4.39 | (1H, d, J = 8Hz), |
| 3.87 | (1H, dd, J = 2 and 12Hz), |
| 3.70 | (1H, dd, J = 5 and 12Hz), |
| 3.4–3.2 | (4H, m), |
| 3.18 | (1H, t, J = 8Hz), |
| 3.10 | (1H, s), |
| 2.73 | (1H, d, J = 17Hz), |
| 2.26 | (1H, d, J = 17Hz), |
| 2.2–1.7 | (9H, m), |
| 1.6–1.4 | (2H, m), |
| 1.35–1.1 | (2H, m), |
| 2.09 | (3H, s), |
| 1.38 | (3H, s), |
| 1.20 | (3H, s), |
| 1.16 | (3H, s), |
| 1.13 | (3H, s), |
| 1.11 | (3H, s), |
| 0.98 | (3H, d, J = 7Hz), |
| 0.97 | (3H, s), |
| 0.92 | (3H, d, J = 7Hz) |
| 0.84 | (3H, d, J = 7Hz) |

| (13) $^{13}$C-NMR spectrum (100 MHz, CD$_3$OD - CDCl$_3$(1:1)): δ | | |
|---|---|---|
| 217.2 (s), | 47.2 (d), | 21.0 (t), |
| 175.2 (s), | 46.1 (t), | 19.3 (t), |
| 172.6 (s), | 43.1 (s), | 18.7 (q), |
| 135.2 (s), | 41.6 (s), | 17.7 (q), |
| 132.5 (s), | 41.3 (t), | 16.8 (q), |
| 105.1 (d), | 39.1 (s), | 10.4 (q) |
| 88.7 (d), | 38.6 (s), | |
| 77.4 (d), | 30.4 (t), | |
| 76.7 (d), | 28.5 (q), | |
| 75.1 (d), | 27.6 (t), | |
| 71.4 (d), | 27.1 (d), | |
| 71.3 (d), | 25.9 (q), | |
| 62.7 (t), | 24.8 (q), | |
| 54.6 (s), | 22.0 (q), | |
| 53.1 (d), | 21.7 (q), | |
| 50.9 (d), | 21.2 (q), | |

From the above physicochemical properties and further investigations, chemical structure of the WF11605 is determined as follows.

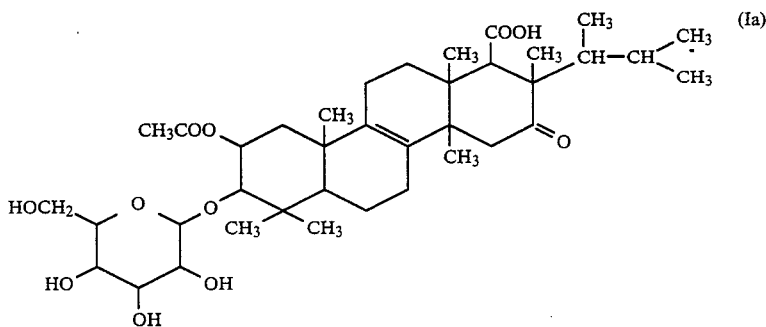

WF11605 can be prepared by culturing a WF11605-producing microorganism in a nutrient medium and recovering the resultant WF11605 from the cultured broth.

Among a WF11605-producing microorganism, Agonomycetes strain F-11605 was newly isolated from a soil sample by inventors of this invention.

Living cultures of the fungus strain F-11605 have been deposited with one of the International Depository Authority on the Budapest Treaty, Fermentation Research Institute, Agency of Industrial Science and Technology at 1-3, Higashi 1 chrome, Tukuba-shi, Ibaraki-ken 305, Japan since Feb. 10, 1988 and were assigned the deposit number FERM BP-1730.

It is to be understood that the production of WF11605 is not limited to the use of the particular organism described herein, which is given for illustrative purpose only. This invention also includes the use of any mutants which can be prepared from the described organism by conventional means such as X-rays, ultra-violet radiation, treatment with N-methyl-N′-nitro-N-nitrosogunidine, 2-aminopurine and the like.

The Agonomycetes strain F-11605 has the following microbiological characteristics.

The Agonomycetes strain F-11605 was originally isolated from a soil sample collected at Kawamata Town, Fukushima Prefecture, Japan. This organism grew rather restrictedly on various culture media, and formed yellowish white to orange white colonies. During two months, the strain formed neither teleomorph nor anamorph. The differentiated hyphal structures (e.g. sclerotia, bulbils, chlamydospores, and clamp connections) were also not observed. These characteristics showed that the strain F-11605 was classified the Agonomycetes (Deuteromycotina)[1], [2]. Its mycological characteristics were as follows.

Cultural characteristics on various agar media were shown in Table 1. Cultures on corn meal agar grew rather restrictedly, attaining 3.0–3.5 cm in diameter after two weeks at 25° C. This colony surface was plane, thin, lustrous and subhyaline to yellowish white. The reverse color was the same. Aerial mycelia and fruiting structures were not obserbed. Vegetative hyphae were septate, straight or flexuous, hyaline, smooth and branched. the hyphal cells were filamentous or cylindrical, and 1–3 μm thick. After four weeks of the inoculation, the cultures reached a diameter of 5.5 cm. Its characteristics were similar to those of two weeks-cultured colonies, but the vegetative hyphae often autolyzed, especially near the center. Colonies on malt extract agar grew the similar rate as on corn meal agar. The surface was plane, lustrous, white to pale yellow, and wrinkly at the center. The sporocarps were not produced. The reverse was pale yellow. On this medium, hyphal cells were rather wider than those on corn meal agar (2–5 μm thick), and did not autolyze after four weeks.

For inducing the strain to sporulate, we attempted several tests: (1) inoculating to a steam-sterilized flat piece of leaf affixed to a corn meal agar plate (Matsushima's method); (2) culturing on agar media containing some differentiation factors (e.g. cAMP, dibutyryl cAMP etc.); (3) throwing a piece of cultures into sterile water; etc. But we were not able to observe the characteristic morphogenesis of strain F-11605, after all.

The strain F-11605 was able to grow at the temperature range from 10° to 33° C. with the growth optimum at 23° to 28° C. These temperature data were determined on potato dextrose agar. This strain grew at pH 4 to 10, and had a growth optimum at pH 6 to 7 in YM broth (Difco).

We named the producing strain to "Agonomycetes strain F-11605".

TABLE 1

| Cultural characteristics of the strain F-11605 | |
|---|---|
| Medium | Cultural characteristics |
| Malt extract agar (Blakeslee 1915) | G: Rather restrictedly, 3.0–3.5 cm<br>S: Circular, plane, wrinkly at the center, Lustrous, not fored aerial mycelium, White to pale yellow (4A3)<br>R: Pale yellow (4A3) |
| Potato dextrose agar (Difco 0013) | G: Rather restrictedly, 3.0–3.5 cm<br>S: Circular, plane, lustrous, poorly formed aerial mycelium, Orange white (6A2)<br>R: Pale yellow (4A3) |
| Czapeck's solution agar (Raper & Thom 1949) | G: Very restrictedly, 1.0–1.5 cm<br>S: Irregular, plane, thin submerged, Lustrous, not formed aerial mycelium, Subhyaline to white<br>R: Subhyaline to White |
| Sabouraud dextrose agar (Difco 0109) | G: Rather restrictedly, 3.0–3.5 cm<br>S: Circulate, plane, wrinkly at the center, Lustrous, poorly formed aerial mycelium, Light orange (6A4)<br>R: Light orange (6A5) |
| Oatmeal agar (Difco 0552) | G: ather restrictedly, 3.0–3.5 cm<br>S: Circular, plane, wrinkly at the center, Poorly formed aerial mycelium, Orange white (6A2), grayish orange (6B3)<br>R: Light orange (6A4), produced pale orange soluble pigments |
| Emerson Yp Ss agar (Difco 0739) | G: Rather restrictedly, 3.0–3.5 cm<br>S: Circular, plane, felty, wrinkly at the margin, White, orange white (6A2)<br>R: Pale orange (5A3), produced pale orange soluble pigments |
| Corn meal agar | G: Rather restrictedly, 3.0–3.5 cm |

TABLE 1-continued

| Medium | Cultural characteristics of the strain F-11605 |
| --- | --- |
| | Cultural characteristics |
| Difco 0386) | S: Circular, plane, thin, submerged, Lustrous, not formed aerial mycelium, Subhyaline to yellowish white (4A2)<br>R: Subhyaline to yellowish white (4A2) |
| My20 agar | G: Rather restrictedly, 3.0–3.5 cm<br>S: Circular, plane, wrinkly, poorly formed aerial mycelium, White, grayish orange (5B3)<br>R: Light yellow (4A4) |

Abbreviation
G: Growth, measuring colony sizes in diameter,
S: Colony surface,
R: Reverse These characteristics were observed after 14 days of incubation at 25° C. The color descriptions were based on the Methuen Handbook of Colour (3).

Literatures:
(1) Arx, J. A. von The Genera of Fungi-Sporulating in pure Culture, J. Cramer, Vaduz, 1974.
(2) Barron, G. L. The Genera of Hyphomycetes from Soil, Williams & Wilkins Co., Baltimore, 1968.
(3) Kornerup, A. and Wanscher, J. H. Methuen Handbook of Colour, Third ed., Methuen, London, 1983.

The WF11605 can be produced by culturing a WF11605-producing microorganism in a nutrient medium containing assimilable sources of carbon and nitrogen, preferable under aerobic conditions (e.g. shaking culture, submerged culture, etc.).

The preferred sources of carbon in the nutrient medium are carbohydrates such as glucose, fructose, glycerin and starch. Other sources which may be included are lactose, arabinose, xylose, dextrin, molasses and the like.

The preferred sources of nitrogen are yeast extract, peptone, gluten meal, cottonseed flour, soybean meal, corn steep liquor, dried yeast, etc., as well as inorganic and organic nitrogen compounds such as ammonium salts (e.g. ammonium nitrate, ammonium sulphate, ammonium phosphate, etc.), urea, amino acid and the like.

The carbon and nitrogen sources, though advantageously employed in combination, need not be used in their pure form because less pure materials which contain traces of growth factors and considerable quantities of mineral nitrients, are also suitable for use. When desired, there may be added to medium such mineral salts as calcium carbonate, sodium or potassium phosphate, sodium or potassium iodide, magnesium salt, cobalt chloride and the like.

If necessary, especially when the culture medium is foamed remarkably, a defoaming agent such as liquid paraffin, higher alcohol, plant oil, mineral oil and silicones may be added.

As conditions for the production in massive amounts, submerged aerobic cultural condition is preferred for the production of the WF11605.

For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the object compounds. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. As the medium, in which the vegetative inoculum is produced, there can be used substantially the same as or somewhat different medium from medium utilized for main production of the object compounds.

Agitation and aeration of the culture mixture may be accomplished in a variety of ways. Agitation may be provided by a propeller or the similar mechanical agitation equipment, by revolving or shaking the fermenter, by various pumping equipment or by the passage of sterile air through the medium. Aeration may be effected by passing sterile air through the fermentation mixture.

The fermentation is usually conducted at a temperature about between 20° C. and 40° C., preferably around 28° C., for a period of 50 hours to 100 hours, which may be varied according to the fermentation conditions and scale.

Thus produced WF11605 can be recovered from the culture broth by conventional means which are commonly used for the recovery of other fermentation products such as antibiotics.

In general, the produced WF11605 are found both in cells and culture medium and accordingly the object compound can be isolated from the cultured broth in a conventional method such as concentration under reduced pressure, lyophilization, extraction with a conventional solvent (e.g. acetone), pH adjustment, treatment with a conventional resin (e.g. anion or cation exchange resin, non-ionic adsorption resin), treatment with a conventional adsorbent (e.g. activated charcoal, silicic acid, silica gel, cellulose, alumina), crystallization, recrystallization and the like.

The WF11605 as obtained in its free form may be converted to a salt with inorganic or organic base such as sodium salt, potassium salt, triethylamine salt and the like.

The derivatives of the WF11605 can be prepared by the following process.

Process 1:

-continued
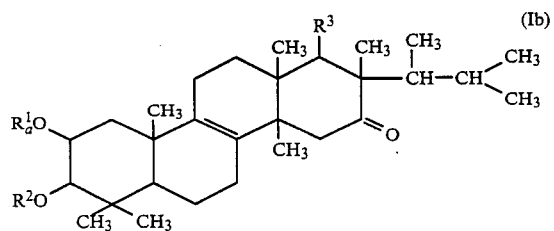
or salt thereof
↓ Hydrolysis
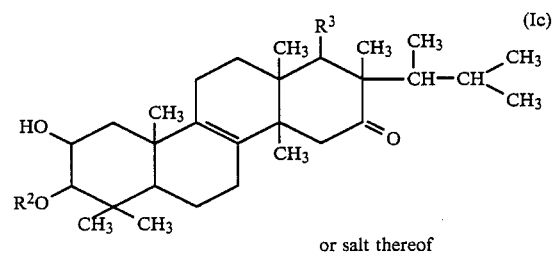
or salt thereof
Process 2:
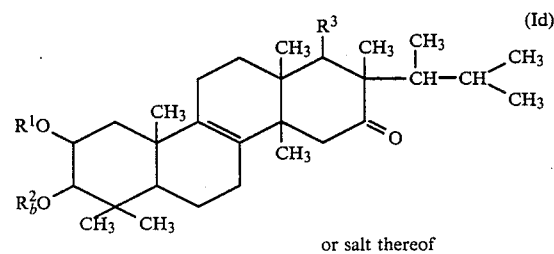
or salt thereof
↓ Acylation
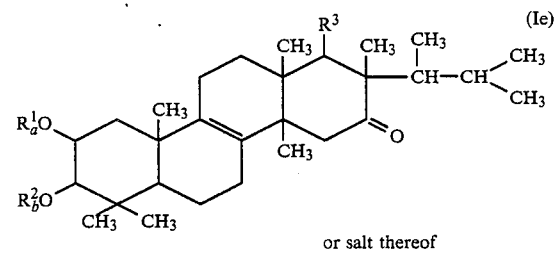
or salt thereof
Process 3:
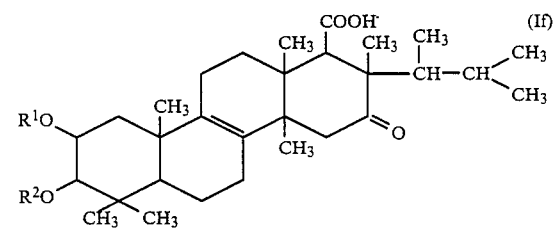
or salt thereof
↓ Introduction of the carboxy-protective group -continued (Ig)

[Chemical structure diagram]

wherein
R¹, R² and R³ are each as defined above,
$R_a^1$ is acyl,
$R_a^2$ is

[Chemical structure with HOCH₂, HO, OH, OH]

$R_b^2$ is

[Chemical structure with $R_a^4OCH_2$, $R_a^5O$, $OR_a^6$, $OR_a^7$]

in which $R_a^4$, $R_a^5$, $R_a^6$ and $R_a^7$ are each acyl, and $R_a^3$ is a protected carboxy.

In the above and subsequent descriptions of this specification, suitable examples and illustrations of the various definitions are explained in detail in the followings.

The term "lower" is intended to means 1 to 6 carbon atom(s), unless otherwise indicated.

The "acyl" may include the residue of organic acid such as organic carboxylic acid, organic sulfonic acid, organic carbamic acid, organic carbonic acid and the like.

Suitable "acryl" may be alkanoyl such as lower alkanoyl (e.g. formyl, acetyl, propionyl, butyryl, isobutyryl, 3,3-dimethylbutyryl, valeryl, isovaleryl, pivaloyl, hexanoyl, etc.) and the like.

The "protected carboxy" is carboxy protected by a conventional carboxy-protective group and suitable example thereof may include an esterified carboxy such as lower alkoxycarbonyl (e.g. methoxycarbonyl, ethoxycarbonyl, propoxycarbonyl, butoxycarbonyl, pentyloxycarbonyl, etc.).

The salts of the compounds (Ib), (Ic), (Id), (Ie) and (If) may include the same as pharmaceutically acceptable salt of the compound (I) as exemplified above.

The process as illustrated above are explained in more detail in the followings.

PROCESS 1:

The compound (Ic) or salt thereof can be prepared by hydrolyzing the compound (Ib) or salt thereof.

The hydrolysis is usually carried out in the presence of an inorganic or organic base such as alkali or alkaline earth metal hydroxide (e.g. sodium hydroxide, etc.) or an inorganic or organic acid such as an mineral acid (e.g. hydrochloric acid).

In this process, when the hydrolysis is carried out in the presence of the base, only acyl group(s) of the compound (Ib) is removed under ordinary conditions and when the hydrolysis is carried out in the presence of the acid, both acyl group(s) and a group of the formula:

[Chemical structure with $R^4OCH_2$, $R^5O$, $OR^6$, $OR^7$]

of the compound (Ib) are removed under ordinary conditions.

This reaction is usually carried out in a solvent which does not adversely influence the reaction (e.g. methanol, tetrahydrofuran, etc.).

The reaction temperature is not critical and the reaction can be carried out under heating to under cooling.

PROCESS 2:

The compound (Ie) or salt thereof can be produced by acylating the compound (Id) or salt thereof with an acylating agent.

The acylating agent to be used in this reaction includes an organic acid (i.e. $R^8$-OH(II), in which R is acyl) and its reactive derivative.

The suitable reactive derivative of the compound (II) may be a conventional one such as an acid halide (e.g. acid chloride, acid bromide, etc.), an acid azide, an acid anhydride, an activated amide, an activated ester, an isocyanate and the like.

When free acid is used as an acylating agent, the acylating reaction may preferably be conducted in the presence of a conventional condensing agent.

The reaction can preferably be conducted in the presence of an organic or inorganic base.

This reaction is usually carried out in a solvent which does not adversely influence the reaction such as methanol, ethanol, propanol, tetrahydrofuran, chloroform and the like.

(a) Preparation of rabbit PMNLs

PMNLs were collected from the peritoneal exudates of male Japanese White rabbits. At 16 hr after the injection of 0.1% glycogen (400 ml/animal, i.p.), the peritoneal cells were collected and washed with Eagle's minimum essential medium (MEM) and resuspended in the same medium. Over 90% of the cells were judged as PMNLs after Giemsa staining.

(b) Assay of PMNLs degranulation

PMNL suspension ($5 \times 10^6$ cells/ml) was incubated with test substance or vehicle at 37° C. for 5 min in plastic tubes. Leukotriene B₄ (LTB₄, $7 \times 10^{-8}$M, Cayman Chemical Co.,), N-formyl-L-methionyl-L-phenylalanine (FMLP, $7 \times 10^{-10}$M, Sigma) or platelet activating factor (PAF, $7 \times 10^{-7}$M, Sigma) together with Cytochalasin B ($10^{-5}$M, Sigma) were added and then incubated for 5 min at 37° C. Incubation was terminated by transfer to an ice bath followed by rapid centrifugation. The cell-free supernatants were subsequently assayed for the activity of beta-glucuronidase.

(c) Beta-glucuronidase assay

The assay mixture consisted of 300 $\mu$l of acetate buffer (0.1M, pH 4.6), 100 $\mu$l of sample (supernatant obtained above) and 50 $\mu$l of methylumbelliferyl-beta-D-glucuronide (1 mM, NAKARAI CHEMICAL Co.,) as substrate. The reaction was started by addition of the substrate and terminated after 15 min at 37° C. by the addition of 2 ml glycine buffer (0.1M, pH 10.32). The fluorescence (excitation; 365 nm, emission; 455 nm) of each sample was determined.

The results are expressed as percent of total beta-glucuronidase released where total are the amount of the enzyme in the cells released by 0.1% Triton X-100.

| Effect of WF11605 on LTB$_4$-induced degranulation in rabbit PMNLs | |
|---|---|
| WF11605 (M) | Inhibition of total beta-glucuronidase release (%) |
| 0 | — |
| $10^{-8}$ | 12.2 |
| $10^{-7}$ | 17.5 |
| $10^{-6}$ | 30.3 |
| $10^{-5}$ | 66.9 |
| $10^{-4}$ | 93.6 |

| Inhibitory effect of WF11605 on LTB$_4$-, FMLP- or PAF-induced degranulation | | | |
|---|---|---|---|
| | LTB$_4$ | FMLP | PAF |
| WF11605 (M) | $3 \times 10^{-6}$ | $>10^{-4}$ | $>10^{-4}$ |

Each value was expressed as 50% inhibitory concentration (IC$_{50}$).

TEST 1

[Inhibition of binding of $^3$H-LTB$_4$ to freeze-thawed PMNLs by WF11605]

(a) Preparation of freeze-thawed PMNLs

PMNLs collected from the peritoneal exudate of rabbit were suspended at a concentration of $5 \times 10^6$/ml in Eagle's MEM, stored at $-20°$ C. and used within 2 weeks. On use, the PMNLs were thawed at room temperature and kept at 4° C.

(b) $^3$H-LTB$_4$ receptor assay $^3$H-LTB$_4$((5,6,8,9,11,14,15 (n)-$^3$H)Leukotriene B$_4$, 20 $\mu$Ci/ml, Amersham Co., Japan) was diluted 20-fold with $3 \times 10^{-9}$M nonradioactive LTB$_4$ in Hanks' balanced salt solution containing 10 mM N-(2-Hydroxyethyl)-piperazine-N'-2-ethanesulfonic acid, pH 7.4 (HBSS-HEPES). Fifteen microlitter of the solution was added to 60 $\mu$l HBSS-HEPES at 4° C. and then 25 $\mu$l of competitor or corresponding vehicle and 150 $\mu$l of freeze-thrawed cells ($5 \times 10^6$/ml) were also added, followed by vigorous mixing and allowing to stand for 30 min at 4° C. The resultant mixture was immediately filtered through Whatman GF/C glass filter to separate free and bound $^3$H-LTB$_4$ using cell harvester (BRANDELL M-24R 5/8). The filter paper was quickly washed 5 times by 150 $\mu$l of cold HBSS-HEPES, dried, cut off and placed in a scintillation vial. To the vial was added 3 ml of toluene-based scintillation fluid and then the radioactivity was counted. All assay were carried out in duplicate. Specific binding defined as total binding minus non specific binding (with 0.1 $\mu$M LTB$_4$), was about 60% of total binding.

| Inhibition of WF11605 on $^3$H-LTB$_4$ binding to rabbit PMNLs | | |
|---|---|---|
| WF11605 (M) | $^3$H-LTB$_4$ specific binding (dpm) | inhibition of 3H-LTB$_4$ specific binding (%) |
| 0 | 1684 | — |
| $7 \times 10^{-7}$ | 1264 | 24.9 |
| $7 \times 10^{-6}$ | 596 | 64.6 |

TEST 2

[Antimicrobial activity of WF11605]

Antimicrobial activity of WF11605 was determined by broth dilution method in a conventional manner. The results show that WF11605 has antimicrobial activity against certain yeasts.

| Microorganism | MIC ($\mu$g/ml) |
|---|---|
| *Candida albicans* FP633[1] | 25 |
| *Candida krusei* OUT-6007[1] | 25 |
| *Candida utilis*[1] | 50 |
| *Cryptococcus albidus* AHU-3922[1] | 100 |
| *Torulopsis colliculsa* IAM-4426[1] | 50 |
| *Mucor rouxianus* Wehmer[2] | 200 |

[1]Sabouraud 30° C. 20 hrs
[2]Sabouraud 25° C. 40 hrs

TEST 3

[Acute toxicity]

The WF11605 was intraperitoneally given to mice (female, 4 weeks old). From the test results, LD$_{50}$ of WF11605 was more than 1 g/kg.

The compound (I) and pharmaceutically acceptable salt thereof are antibiotics and antagonists of LTB$_4$ and therefore useful as an antimicrobial agent and a medicine for preventing and treating diseases caused by LTB$_4$ such as myocardial infraction, hepatitis, rheumarthritis, gout, arteriosclerosis, psoriasis and the like.

The compound (I) and pharmaceutically acceptable salt thereof in admixture with pharmaceutically acceptable carriers can be administered orally or parenterally to mammals including human being in a form of a pharmaceutical composition such as capsules, tablets, granules, powders, buccal tablets, sublingual tablets, and solutions.

The pharmaceutically acceptable carriers may include various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropyl-starch, sodium glycolestarch, sodium bicarbonate, calcium phosphate, calcium citrate, etc.), lubricant (e.g. magnesium stearate, aerosil, talc, sodium laurylsulfate, etc.), flavoring agent (e.g.

citric acid, mentol. ammonium salt of glycyrrhizin, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent [e.g. surface active agent, etc.], aqueous diluting agent (e.g. water), base wax (e.g. cacao butter, polyethyleneglycol, white petrolatum, etc.).

A dosage of the object compounds is to be varied depending on various factors such as kind of diseases, weight and/or age of a patient, and further the kind of administration route.

The optimal dosage of the compound (I) is usually selected from a dose range of 1 mg–1 g/day, preferably 10 mg–500 mg/day.

The total daily amount mentioned above may be divisionally given to the patient at the interval of 6–12 hours per day.

The following Examples are given for the purpose of illustrating this invention.

EXAMPLE 1

(1) Fermentation

An aqueous seed medium (100 ml) containing 2% of soluble starch, 1% of cron starch, 1% of glucose, 1% of cottonseed meal, 1% of dried yeast, 0.5% of polypeptone, 0.5% of corn steep liquor and 0.2% of calcium carbonate (pH was adjusted 6.0 with 6N aqueous sodium hydroxide) was poured into each of three 500 ml Erlenmeyer flasks and sterilized at 125° C. for 30 minutes. A loopful of Agonomycetes strain F-11605 on mature slant culture was inoculated to each of the seed medium. The flasks were shaken on a rotary shaker (220 rpm, 5.1 cm throw) at 25° C. for 5 days. The resultant seed culture was inoculated to 20 l sterile fermentation medium containing 3% of soluble starch, 1% of glucose, 1% of wheat germ, 0.5% of cottonseed meal and 0.2% of calcium carbonate in 30 l stainless steel jar-fermentor. The fermentation was carried out at 25° C. for 5 days under aeration of 20 l/min and agitation of 200 rpm.

An amount of WF11605 in the fermentation broth was quantified by standard disk-agar diffusion assay, using *Candida albicans* as a test organism. The sample for the bioassay was prepared as follows; an equal volume of acetone was added to a broth with vigorous stirring and allowed to stand for 1 hr and then filtered. The filtrate was concentrated under reduced pressure to an appropriate volume.

(2) Purification

An equal volume of acetone was added to the culture broth (18 l) with stirring. The mixture was allowed to stand at room temperature overnight and then filtred. The filtrate was concentrated to 1 litter under reduced pressure, and was adjusted to pH 2.0 with 1N hydrochloric acid, and then extracted with 2 l of ethyl acetate. The extract was concentrated to dryness under reduced pressure and applied to a column of silica gel (Silicar CC-4, Mallinckrodt, 800 ml). The column was washed with n-hexane (1 l), ethyl acetate (1 l), and the active substance was eluted from the column with acetone (2 l). The active fractions were dried under reduced pressure, and was subjected to a column chromatography on silica gel (Kiesel gel 60, Merck, 250 ml). The object substance was eluted with a solution of chloroform-methanol-acetic acid (200:20:1 V/V, 80 ml). The fraction was dried under reduced pressure to give a powder (150 mg). The powder was dissolved in a small volume of methanol and allowed to stand overnight at 4° C. to give colorless crystal (105 mg) of WF11605.

(3) Purification

An equal volume of acetone was added to the culture broth (16 l) obtained in the above (1) with stirring and allowed to stand at room temperature overnight and then filtered. A half volume of water (14 l) was added to the filtrate (28 l). The solution (42 l) was adjusted to pH 3.0 with 6N hydrochloric acid and then passed through a column of nonionic adsorption resin, Diaion HP-20 (trademark, made by Mitsubishi Chemical Industries Limited, 1.2 l). The column was washed with 30% aqueous acetone solution (3.6 l), and eluted with 75% aqueous acetone (3.6 l). The eluate was concentrated under reduced pressure to a volume of 800 ml. The resultant solution was extracted with an equal volume of ethyl acetate (800 ml). The extract was concentrated and dried under reduced pressure to give a residue, which was subjected to a column chromatography on silica gel (Kiesel gel 60, Merck 200 ml) using a solution of chloroform-methanol-acetic acid (200:20:1, V/V) as an eluent. The first fraction (~300 ml) was discarded and second fraction (300–400 ml) was collected and concentrated under reduced pressure to give crystals, which were collected by filtration and dried. Thus obtained product was purified by recrystallization from methanol to give colorless needle of WF11605 (70 mg).

EXAMPLE 2

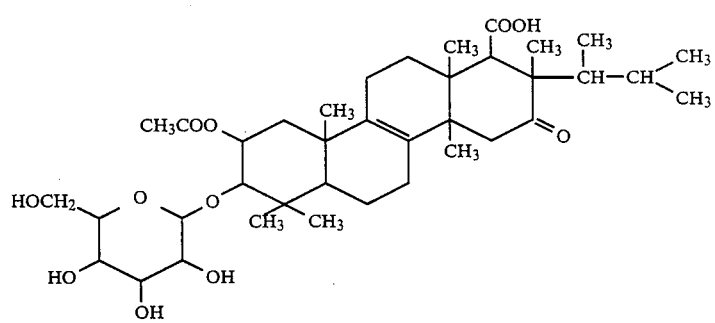

-continued

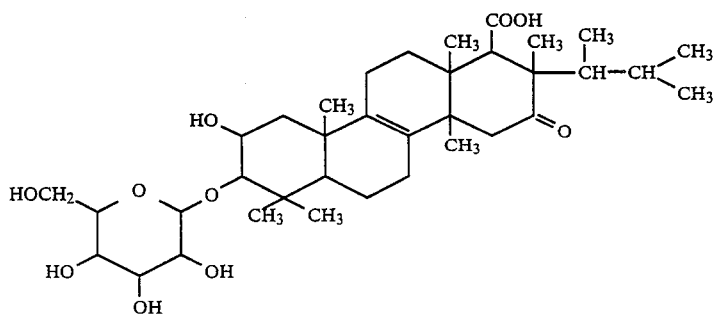

A mixture of the WF11605 (300 mg), 1N aqueous hydroxide (1.73 ml), tetrahydrofuran (3 ml) and methanol (3 ml) was stirred at 20° C. overnight. The reaction mixture was poured into 1N hydrochloric acid, and the precipitates were collected by filtration, washed with water and ether, and recrystallized from ethanol to give deacetate of WF11605 (210 mg).

mp: 288°–290° C.
IR (Nujol): 3400, 1735, 1695, 1665 cm$^{-1}$.

EXAMPLE 3

A solution of the WF11605 (300 mg) in 20% hydrogen chloride-methanol (30 ml) was refluxed with stirring for 3 hours and evaporated to dryness in vacuo. The residue was partitioned between ethyl acetate and water. The organic layer was dried over magnesium sulfate and evaporated to dryness in vacuo to give a powder. The powder was subjected to a silica gel column chromatography [developing solvent: chloroform-methanol (20:1)] to give deacetyl-aglycon of the WF11605 (200 mg) as colorless powder.

$[\alpha]_D^{23}$: $-15°$ (C=0.5, CH$_3$OH).
FAB-MS: m/z 511 (M+Na)
IR (Nujol): 3350, 2920, 1710, 1680, 1380 cm$^{-1}$.

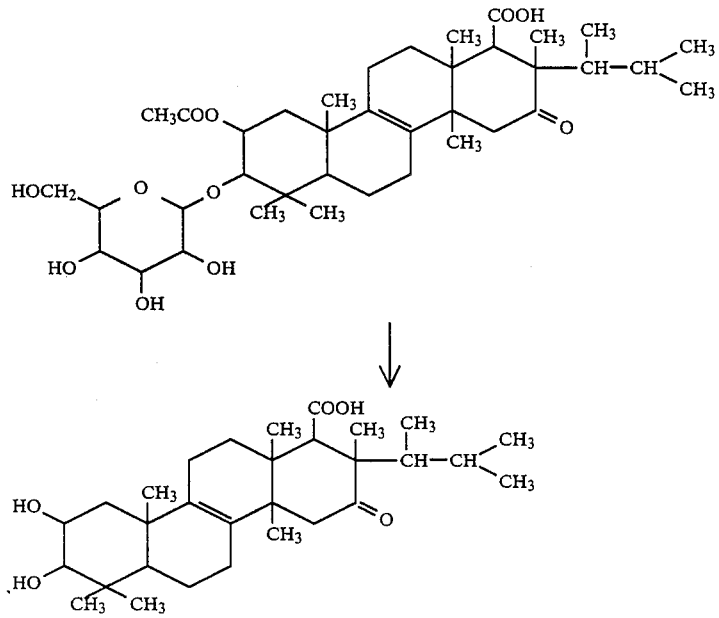

EXAMPLE 4

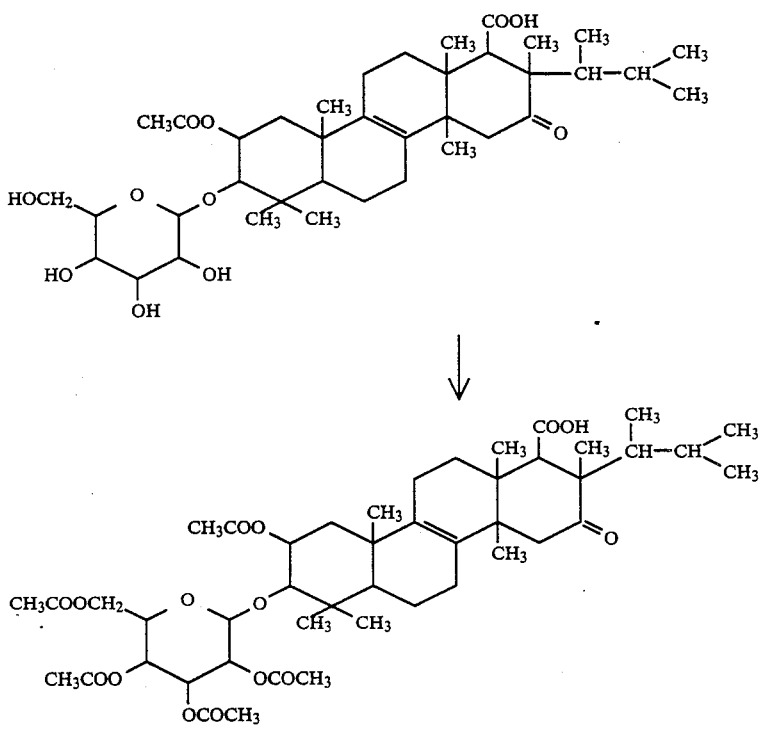

A mixture of WF11605 (100 mg), acetic anhydride (0.271 ml) and pyridine (1 ml) was stirred at 20° C. overnight. The mixture was poured into a mixture of ethyl acetate and diluted hydrochloric acid. The organic layer was separated, washed with water and brine, dried over magnesium sulfate, and evaporated in vacuo. The crystalline residue was wahed with ethyl acetate and dried to give the tetraacetate of the WF11605 (102 mg).

mp: 138°–142° C.
IR (Nujol): 3480, 3330, 3240, 1770, 1750, 1735, 1710, 1620, 1590 cm$^{-1}$.

EXAMPLE 5

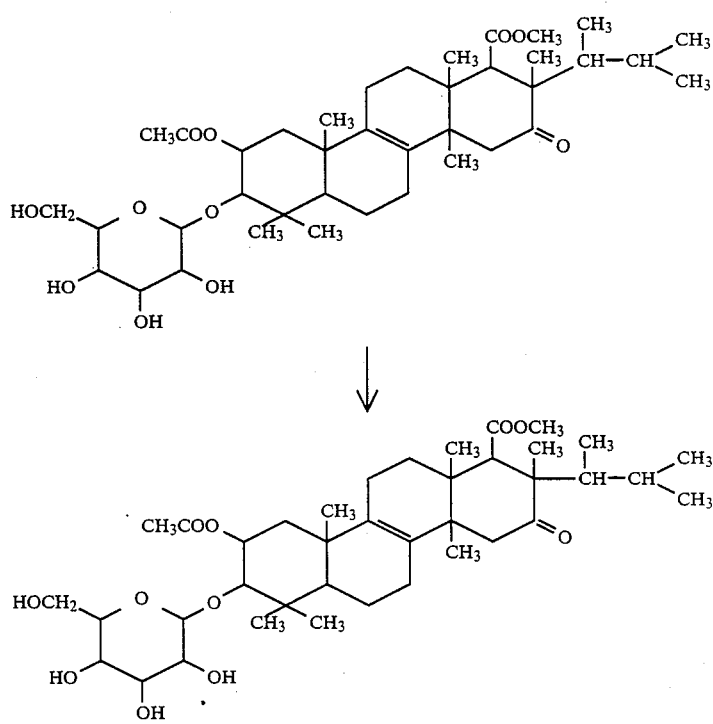

A solution of diazomethane in ether was added to a solution of the WF11605 (1.0 g) in a mixture of methanol and chloroform (1:1)(20 ml) until the yellow color of diazomethane was still remained. The solvent was evaporated off in vacuo and the crystalline residue was washed with ether to give the methyl ester of the WF11605 (1.0 g).

mp: 291°–295° C.

IR (Nujol): 3480, 1725, 1685 cm$^{-1}$.

We claim:

1. A compound of the formula:

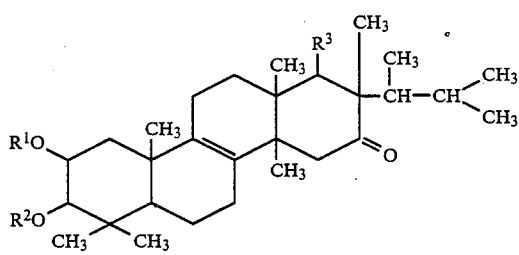

wherein $R^1$ is hydrogen or lower alkanoyl, $R^2$ is hydrogen or

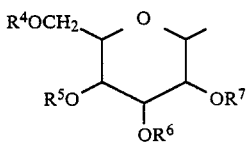

in which $R^4$, $R^5$, $R^6$ and $R^7$ are hydrogen or lower alkanoyl, $R^3$ is carboxy or a protected carboxy, and pharmaceutically acceptable salt thereof.

2. A compound of claim 1, in which
$R^1$ is hydrogen or lower alkanoyl,
$R^3$ is carboxy or lower alkoxycarbonyl, and
$R^4$, $R^5$, $R^6$ and $R^7$ are hydrogen or lower alkanoyl.

3. A compound of claim 2, in which
$R^1$ is hydrogen or acetyl,
$R^3$ is carboxy or methoxycarbonyl, and
$R^4$, $R^5$, $R^6$ and $R^7$ are hydrogen or acetyl.

4. A compound of claim 3, in which
$R^1$ is acetyl,
$R^4$, $R^5$, $R^6$ and $R^7$ are hydrogen and
$R^3$ is carboxy.

5. A pharmaceutical composition comprising the compound (I) of claim 1 or pharmaceutically acceptable salt thereof and nontoxic, pharmaceutically acceptable carrier(s).

* * * * *